United States Patent [19]

Chesnut

[11] Patent Number: 4,823,556
[45] Date of Patent: Apr. 25, 1989

[54] ELECTRONIC ICE BANK CONTROL

[75] Inventor: Milton L. Chesnut, San Antonio, Tex.

[73] Assignee: Lancer Corporation, San Antonio, Tex.

[21] Appl. No.: 51,080

[22] Filed: May 15, 1987

[51] Int. Cl.[4] .............................................. F25C 1/00
[52] U.S. Cl. ........................................ 62/139; 62/201; 62/228.2
[58] Field of Search .................. 62/137, 138, 139, 140, 62/126, 127, 128, 129, 130, 201, 228.2; 340/580, 601, 602

[56] References Cited

U.S. PATENT DOCUMENTS

| | | | |
|---|---|---|---|
| 3,496,733 | 2/1970 | Parker et al. ........................ | 62/139 |
| 3,502,899 | 3/1970 | Jones .................................. | 62/139 X |
| 3,782,130 | 1/1974 | Irvine ................................. | 62/128 |
| 4,333,004 | 6/1982 | Forgue et al. .................... | 340/580 X |
| 4,497,179 | 2/1985 | Iwans ............................... | 62/139 X |
| 4,655,050 | 4/1987 | Aschberger et al. ............. | 62/139 X |

Primary Examiner—Harry B. Tanner
Attorney, Agent, or Firm—Cox & Smith Incorporated

[57] ABSTRACT

A method and apparatus for controlling the growth of the solid phase of a substance from around a cooling mechanism, such as the growth of an ice pack in a water cooling system, while also minimizing chances of inaccurate control by referencing the apparent resistance of the liquid that is actually in the system rather than a standard value. The method also provides for a deadband by monitoring the resistance of the liquid at two roughly adjacent locations.

4 Claims, 1 Drawing Sheet

ELECTRONIC ICE BANK CONTROL

BACKGROUND OF THE INVENTION

The present invention pertains to a method for sensing the phase transformation of a liquid into a solid and vice versa More particularly, the invention pertains to a method for determining when a solid phase of a material has formed at a location submerged in the material, which method depends upon the fact that the electrical resistance of the liquid and solid phases of a substance differ. Although the present invention is effective for monitoring any substance whose solid phase has an electrical resistance different from the electrical resistance of the liquid phase (believed to be true of virtually all substances), it is primarily directed for monitoring phase changes in water to be used in connection with water cooling systems; the following discussion, accordingly, concentrates on characteristics of such an application.

A common method for determining the progression of ice submerged in liquid water has been to monitor the changing resistance of the water. Because the electrical resistance of ice, solid phase water, is much higher than that of liquid water, such monitoring has enabled fairly accurate determination of the presence of ice. However, numerous problems can arise which can cause, previous methods to provide inaccurate indications. In certain situations, these problems can make successful application of the sensing method impossible.

Variations of this common method are essential in cooling systems such as those which employ a compressor and circulating refrigerant to maintain an ice pack within liquid water, which water might be used directly or circulated about an object for cooling the object. In such systems, the sensing method is part of closed-loop feedback control system which causes the compressor to operate often enough to maintain the water at its freezing point but not often enough to cause excessive ice formation. Since the compressor either operates or is shut off, such a control scheme is usually referred to as an "on-off" or "bank-bang" controller. In such systems, an error signal which causes the compressor to shut off is derived by monitoring the resistance of the water surrounding the cooling coils, which coils may carry refrigerant and thereby remove heat from the water The resistance of the water is then compared with a reference value and, if there is a difference, an error signal is produced In the prior art, the reference value is ordinarily a fixed, standard value believed to correspond to that of liquid water. Usually, while the cooling system is cooling the liquid, the liquid crystalizes progressively and radially outward from the cooling coils. The method is employed to interrupt the cooling cycle when the ice progresses to a predetermined position. The resistance of the water used to produce the error signal, hereinafter called the variable resistance, is maintained at the predetermined position. When the value of the variable resistance rises above the reference value, the previous methods indicate that ice has formed at the predetermined position, and this indication initiates the interruption of the cooling process.

A fundamental characteristic of all on-off controllers is oscillation of the controlled variable about the set point. Since the actuator of such a system is operated in an on-off fashion, environmental influences will cause the controlled variable to deviate from the set point when the actuator is off. This produces an error signal to turn the actuator on until the error signal is reduced to zero, and the cycle repeats. Such cycling is undesirable, however, when it is rapid enough, and the actuator is a mechanical device such as a compressor. Rapid start-stop cycles ("fast-cycling") cause excessive wear to the compressor as well as inefficient use of energy. A well known technique of solving this problem is to incorporate a "dead-band" into the controller. A "dead-band" is a range about which the controlled variable is allowed to deviate from the set point before the actuator is either activated or turned off. This is accomplished by making the set point of the system vary between two values according to whether the actuator is on or off. Thus, when the controlled variable is between the higher and lower set points, there is no change in the previously derived error signal which causes the actuator to either remain on or off. Therefore, the range between the higher and lower set points is effectively a "dead-band." In water cooling applications, precise control of the controlled variable is not necessary since the only objective of the control scheme is to prevent excessive ice formation around the cooling coils. Incorporating a dead-band into the system, therefore, involves no significant disadvantages.

The most basic of previous similar methods for controlling water cooling involves, simply, measuring the electrical resistance between a single probe and a grounded reference. Circuitry or other means are connected to the probe in order to measure this resistance and compare it with a predetermined fixed value of resistance, which value has been previously determined as a standard for water. A fundamental problem with such a method utilizing a single resistance reading is that there is no means for providing a dead-band. Lack of a dead-band causes the afore-mentioned practical problems-the compressor may undergo rapid start-stop cycles ("fast-cycling") when the progression of ice is immediately adjacent the probe. To solve this problem of fast-cycling, a dead-band must be incorporated into the control system by either mechanical or electronic means.

Another previous method involves monitoring resistance sensors from two probes. The utilization of two probes in this latter method effectively provides for a dead-band. A dead-band is achieved by electronically requiring that both probes sense the ice in order to stop the compressor while also requiring that the ice melt off both probes in order to activate the compressor once again. A predetermined value for the resistance of water has invariably been used as a reference value for this and each other of the previous methods. This previous method involves positioning a first of the two probes nearer the cooling coils so that it will ordinarily sense the progression of ice before the second probe and will sense melting after the second probe. The dead-band, therefore, occurs when the first probe senses the ice and when the ice melts from around the second probe. When the system is in this state, the compressor will remain in its previous operating mode, either on or off. If the total volume of the ice pack surrounding the cooling coils is viewed as the controlled variable, this system will cause that variable to oscillate between two set points, represented by ice surrounding the first and both probes, respectively.

Unfortunately, since each of the previous inventions depends on a fixed, predetermined value for the resistance of liquid water, the resulting indications are not always accurate since extraneous and nonstandard factors affect the resistance readings within any tank of water, particularly after extended usage. Most basically, the resistance of water may vary in different geographical locations due to local impurities in the water, which impurities generally raise the resistance of water. Resistance of the liquid water may similarly change within a system over time due to evaporation of the water, which evaporation raises the amount of impurities per volume of water remaining. Increased resistance of liquid water is also caused by increased amounts of impurities within the system due to accumulation over time. Employment of similar methods also creates problems in systems where the impurity content of the liquid water or the identity of the liquid is purposefully altered; in such situations the reference value must be changed, thus causing delays, particularly when circuitry must be accordingly modified.

Furthermore, deposits on submerged electrical probes, which deposits are natural over time, often affect the resistance measurements. The additional resistance of deposited impurities adds to the resistance which the probe reads, thereby raising the apparent resistance of the water. With the passage of time, coatings of such impurities inevitably adhere to virtually any probe which is submerged in liquid water that is the slightest bit impure. Notably, these coatings tend to be of uniform thickness on surfaces that are subjected to similar environments. Electrolytical plating on the probes may also affect the apparent resistance of the water as recorded by such probes. The electrolytical type deposits have been minimized with some previous methods by utilizing an alternating current rather than a direct current; however, in practice, slight electrolytical plating still occurs with an alternating current. Electrical probes necessary with every employment of the art, therefore, must be periodically replaced or cleaned when incorporated for use with previous inventions.

Therefore, it is a primary object of the present invention to account for resistance variances of water as well as apparent variances in this resistance caused by impurities deposited on the electrical probes, while providing a method for indicating the phase transformation of liquid water to ice.

Furthermore, previous methods have utilized a grounded electrical reference that is dependent on the system in which the previous method is employed. This presents a particular problem where the method is employed in a container or system that is insulated. It is, therefore, another object of the present invention to incorporate the use of a ground probe which is independent from the system in which the method is employed.

It is another object of the present invention to effectively minimize electrolytical plating and coating of electrical probes utilized with the invention.

It is also an object of the present invention to provide an apparatus which utilizes and enables the method of the present invention.

Additionally, it is an object of the present invention to provide a method for sensing the presence of a solid phase of any material within a liquid phase of any material, including but not limited to water.

It is another object of the present invention to avoid fast-cycling of apparatuses related to any particular employment of the present invention by providing for a dead-band.

These and other objects and advantages will be clear to those skilled in the art who have the benefit of this disclosure from the following detailed description of a preferred embodiment of the present invention.

SUMMARY OF THE INVENTION

Similarly, the method of the present, invention includes monitoring the electrical resistance of a material and comparing the value of that resistance with a reference value for determining the presence of a solid phase within a liquid. The method of the present invention also involves continuously monitoring the apparent resistance of the liquid and using this monitored value as a reference rather than using a predetermined fixed value. The effect of resistance variances in different geographical locations and with the passage of time are, thus, canceler since the variable resistance measured by the controlling probe and the reference resistance measured by the reference probe are dependent on the same liquid. This continuously monitored reference also cancels the effects of probe plating and coating since such effects will be virtually uniform on each of the probes and since the elevated apparent resistance monitored by a controlling probe with deposits thereon will be compensated by an elevated apparent resistance monitored by the reference probe with similar deposits.

Additionally, the present invention provides for alleviating fast-cycling by incorporating provisions for a dead-band. Two controlling probes are used positioned so that the second controlling probe is beside the first controlling probe but at a greater radial distance from the cooling coils. The sensing of ice by both the first and second probes (indicated by increased resistance to ground) turns off the compressor while the sensing of liquid water by both the first and second probes (indicated by the same resistance to ground as from the reference probe) causes the compressor to turn on.

Furthermore, the present invention provides for utilization of a ground probe that is independent from the container or other part of the system that contains the liquid which the method is employed to monitor.

The present invention also utilizes an alternating current rather than a direct current in order to minimize the electrolytical plating effects caused by direct current.

An apparatus for enabling and utilizing the method of the present invention is also included. This apparatus comprises four electrical probes for measuring the reference resistance and two variable resistances as well as providing a common ground. Circuitry is also included for effecting the indications and controls of the present invention.

Other objects, features, and advantages of the invention will become evident in light of the following detailed description considered in conjunction with the referenced drawings of a preferred exemplary instrument according to the present invention.

BRIEF DESCRIPTION OF THE DRAWINGS

FIG. 1 also shows a side view of the probes of the apparatus of the present invention, showing their respective positioning.

DESCRIPTION OF THE PREFERRED EMBODIMENT

Figure 1:
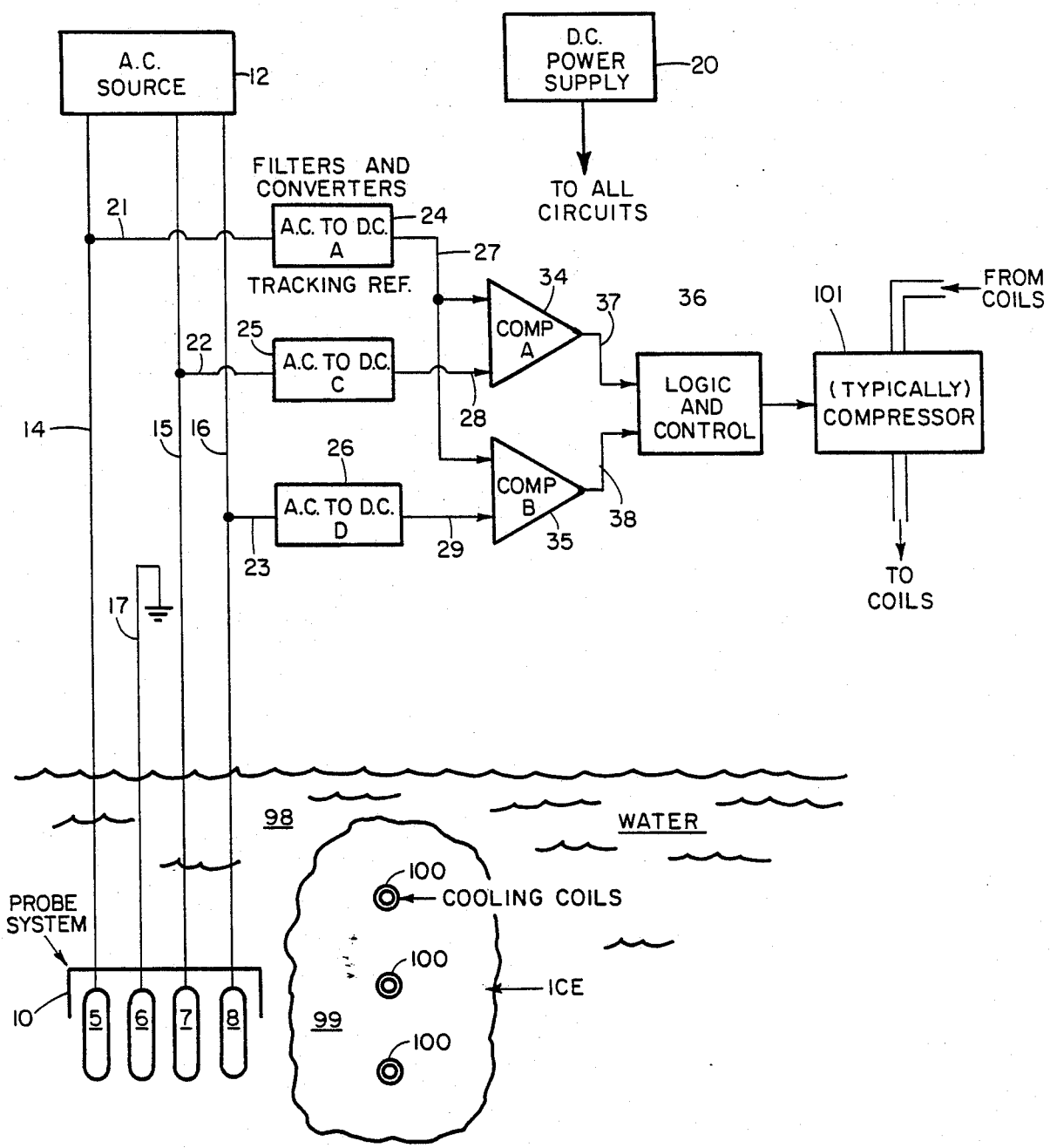
FIG. 1 is a schematic view of the apparatus of the present invention as it would be typically positioned in a common environment.

Referring to FIG. 1, the apparatus of the present invention, which embodies and utilizes the method of the present invention, is shown in conjunction with compressor 101, which compressor effects the cooling of ice pack 99 with condenser coils 100 when compressor 101 is empowered. Compressor 101 is empowered by DC power supply 20 by means which are discussed further in this application. Compressor 101 and cooling coils 100 are components of a cooling system which contains liquid water 98. When the compressor 101 is empowered, ice pack 99 grows in size and the banks of ice pack 99 progress outwardly from coils 100. When the compressor 101 is not empowered, ice pack 99 melts and the banks of ice pack 99 recess inwardly toward coils 100. 1

The apparatus of the present invention comprises probes 5 through 8 positioned in a linear formation equidistantly spaced (as shown in FIG. 1). Probes 5 through 8 are roughly cylindrical in shape. The compositions and dimensions of probes 5 through 8 are similar. Probes 5, 7 and 8 are in electrical communication with the control circuitry of the present invention. Bracket 10, composed of an electrically insulative material, is rigidly connected to probes 5 through 8 for fixing the respective positioning of said probes 5 through 8. Each of probes 5, 7 and 8 are also in electrical communication with means for producing alternating current 12; this operative connection with the alternating current source 12 is for providing alternating current to probes 5, 7 and 8. Probe 6 is a ground probe and is operatively connectable in electrical communication with an appropriate ground G. Probe 6 is a common ground for probes 5, 7 and 8. Insulated conductors 14, 15 and 16 are operatively connected between alternating current source 12 and probes 5, 7 and 8, respectively, in a manner which provides alternating current which is respectively in phase and of equivalent amplitude to each of probes 5, 7 and 8. The peak-to-peak amplitudes of the voltages produced by the alternating current, measured at any point along insulated conductors 14, 15 and 16 are proportional to the resistances between probe 6 and probes 5, 7 and 8 respectively owing to the current amplitude being maintained constant through each insulated conductor.

Converters 24, 25, and 26 are operatively connected in electrical communication with insulated conductors 14, 15, and 16, respectively, by leads 21, 22 and 23, respectively. Each of converters 24, 25 and 26 convert the alternating current to direct current signals, the amplitudes of which are proportional to the peak-to-peak amplitude of the alternating current signals. The rectified alternating current signals are then filtered before inputting to comparators 34 and 35. Converters 24, 25 and 26 are also operatively connectable in electrical communication with DC power supply 20 for enabling the alternating current to direct current conversion. DC power supply 20 is further operatively connectable to alternating current source 12 for receiving alternating current power from alternating current source 12. DC power supply 20 comprises means for transforming the received alternating current power to direct current power to all circuits of the system needing DC power. DC power supply 20 is a common power supply for converters 24, 25, and 26 as well as logic and control unit 36. Converters 24, 25 and 26 are similar in their electrical characteristics.

Leads 27, 28 and 29 are operatively connected in electrical communication with converters 24, 25 and 26, respectively, for conducting the direct current signals from said converters 24, 25 and 26, respectively. Comparator 34 is operatively connected to receive the direct current signals from leads 27 and 28 to compare the signals from leads 27 and 28. Comparator 35 is operatively connected to receive the direct current signals from leads 27 and 29 to compare the signals from leads 27 and 29. Comparators 34 and 35 have similar electrical characteristics. The electrical characteristics of each comparator 34 and 35 are such as to produce a high signal when the compared input signals are different and a low signal when the compared input signals are the same. A high output signal from a comparator therefore indicates the presence of ice around the controlling probe 7 or 8 which inputs into it.

Logic and control unit 36 is operatively connected in electrical communication with comparator 34 and 35 through leads 37 and 38, respectively. Comparator 34 provides an electronic comparison signal to logic and control unit 36 through lead 37. Comparator 35 communicates the appropriate electronic comparison signal to logic and control unit 36 through lead 38.

Logic and control unit 36 comprises appropriate electronic circuitry to analyze the comparison signals that are received through leads 38 and 37. Logic and control unit 36 further includes electronic circuitry for transmitting electrical signals for controlling the operation of the compressor 101. These controlling signals are transmitted through output wires 39. The circuitry of logic and control unit 36 controls the operation of the compressor 101 by means incorporated with logic and control unit 36 for engaging and disengaging the compressor 101 with power from DC power supply 20. Output wires 39 are operatively connected to the circuitry of logic and control unit 36 and are operatively connectable to compressor 101 for enabling electrical communication between logic and control unit 36 and compressor 101.

The circuitry of logic and control unit 36 is such that when both comparators 34 and 35 are producing high signals, corresponding to ice surrounding both probes 8 and 7, the compressor 101 is stopped. When both comparators 34 and 35 produce low signals, corresponding to water surrounding both probes 8 and 7, the compressor is started. Any other combination of outputs from the comparators produce no change in the operating state of the compressor.

In operation, probes 5 through 8 are to be positioned submerged in water or a water based solution, with probe 8 being closest to the origin and likely direction from which ice production will progress. Such a positioning is shown in FIG. 1 as the ice 99 will likely progressively form outwardly from coils 100. Although FIG. 1 displays the present invention employed in a system which contains water, the present invention may also be employed in any system which contains a liquid that transforms into the solid phase, which solid phase has an electrical resistance distinguishable from the electrical resistance of the liquid phase.

Accordingly, when the alternating current is provided by alternating current supply 12 through insulated conductors 14, 15 and 16, current also flows from each of probes 5, 7 and 8 to ground probe 6. The resistance between ground probe 6 and probe 5 is the reference resistance. The resistances between probe 7 and probe 6 and between probe 8 and probe 6 are variable resistances. The substance surrounding probes 5 and 6 is always liquid since, as will be apparent further in this discussion, progression of the bank of the ice pack 99 ceases when the ice pack 99 has surrounded probes 7.

The reference resistance, thus will always correspond to the resistance of the liquid within the system.

The method of the present invention is also schematically represented in FIG. 1. The method of the present invention may utilize an apparatus similar to the apparatus of the present invention. Components of the apparatus of the present invention, thus, are referenced in the description of the preferred method of the present invention. The method involves first selecting positions submerged in the liquid water, which positions are selected to approximate desired volume limits of the ice bank 99. After these predetermined positions are selected, the probes 7 through 8 are situated at the predetermined position with probe 8 positioned nearer the cooling coils 100 than the other probe 7. Probes 6 and 5 are then located at some greater distance from the cooling coils 100. The positioning of probes 5 through 8 is such that an imaginary line through probes 5 through 8 is approximately perpendicular to the closest surface of the ice bank 99. Insulated conductor 17 is connected in electrical communication with an electrically grounded object. Once probes 5–8 are positioned, alternating current source 12 and direct current power supply 20 are operated to empower the electrical circuitry of the apparatus of the present invention. This empowering of the electrical circuitry enables the operation of the apparatus of the present invention.

Thus, as the bank of ice pack 99 progresses, probe 8 is the first of probes 5–8 to be surrounded by ice pack 99. As the bank of the ice pack 99 progresses further, probe 7 is surrounded by ice and the resistance between it and ground probe 6 rises above the reference resistance. Sensing that both comparators have gone high, logic and control unit transmits an electrical signal for interrupting the cooling operation of the compressor 101. The cooling operation of the system is, thus, ceased and ice pack 99 ceases to grow in size. Once the operation of the compressor is interrupted, ice pack 99, accordingly, begins melting. After ice pack 99 has melted from around probe 8, logic and control unit 36 senses that the resistance between it and ground probe 6 is equal to the reference resistance, and logic and control unit 36, accordingly, transmits an electrical signal to compressor 101 for reinitiating the operation of compressor 101. Ice pack 99, subsequently, ceases melting and the bank of ice pack 99 again progresses toward probe 7 again. The operation of the system may be continued in this manner indefinitely to effectively control the size of ice pack 99.

Thus, the operation of the apparatus of the present invention in conjunction with compressor 101 and cooling coils 100 enables, embodies and utilizes the method of the present invention in a preferred manner. This method, basically, includes the steps of selecting a position within the liquid water, which position is desired by the implementer of the method of the present invention to be the approximate limit of the progression of a bank of ice pack 99; empowering the circuitry of the apparatus of the present invention with currents from alternating current source 12 and direct current power supply 20; representing the reference resistance as an electrical signal transmitted through lead 21; representing the variable resistances as electrical signals transmitted through leads 22 and lead 23; filtering each of the electronic signals transmitted through leads 21, 22 and 23 to minimize undesirable electronic characteristics of the signal; converting the electrical signals from leads 21, 22 and 23 to direct current signals with converters 24, 25 and 26 respectively; transmitting these direct current signals from converters 24, 25 and 26 through leads 27, 28 and 29, respectively; comparing and determining the electronic differences between the direct current signal in lead 28 with the direct current signal in lead 27, which comparison is enabled by comparator 34; comparing and determining the electronic differences between the direct current signal transmitted through lead 29 with the direct current signal transmitted through 27, which comparison is enabled by comparator 35; representing the respective differences determined by comparators 34 and 35 as electronic signals and transmitting these signals through leads 37 and 38, respectively; utilizing logic and control unit 36 to determine, from the electronic signals transmitted through leads 37 and 38, the operation of compressor 101 for melting and cooling ice pack 99; and controlling the operation of compressor 101 according to the determinations of logic and control unit 36.

More specifically, the method of determining and controlling the operation of compressor 101 by logic and control unit 36 involves several steps. For demonstration purposes, these steps begin at the initial start-up of compressor 101; however, the method of the present invention may be employed at any stage during the production of ice pack 99. The steps of this determination and control of compressor 101 by logic and control unit 36 basically comprise: engaging compressor 101 with power from DC power supply 20 to initiate operation of compressor 101 and to initiate formation of ice pack 99; determining from the electronic signal transmitted through lead 37 that the resistances between probes 7 and 6 and between probes 8 and 6 are is greater than the reference resistance and, subsequently, interrupting the power supply from DC power supply 20 to compressor 101 to stop the operation of compressor 101 and begin melting ice pack 99; determining from the electronic signal transmitted through lead 38 that the resistances between probes 7 and 6 and between probes 8 and 6 are equal to the reference resistance and, subsequently, reengaging compressor 101 with power from power supply 20 for reinitiating growth of ice pack 99; and continuing the previous steps. By this method, the melting and reinitiating of the growth of ice pack 99 may be continued for as enduring a period of time as is desired by the implementer of the method of the present invention.

Although the invention has been described in conjunction with the foregoing specific embodiment, many alternatives, variations and modifications are apparent to those of ordinary skill in the art. Those alternatives, variations and modifications are intended to fall within the spirit and scope of the appended claims.

What is claimed is:

1. An apparatus for controlling the size of an ice bank around cooling coils immersed in a water bath as part of a refrigeration system comprising:

a first controlling probe immersed in said water bath and located at a distance from said cooling coils representing the minimum desired size of the ice bank;

a second controlling probe immersed in said water bath and located at a distance from said cooling coils representing the maximum desired size of the ice bank;

a ground probe immersed in said water bath and located at a greater distance from said cooling coils than either of said first or second controlling probes;

a reference probe immersed in said water bath and located at a greater distance from said cooling coils than either of said first or second controlling probes;

means for producing a constant current between said first controlling probe and said ground probe, between said second controlling probe and said ground probe, and between said reference probe and said ground probe;

means for measuring the voltage potentials of said first controlling probe, said second controlling probe, and said reference probe as constant current flows from each of said probes to said ground probe;

means for turning said refrigeration system on when the potential of said first controlling probe is equal to the potential of said reference probe; and means for maintaining the refrigeration system in an on condition even as the potential of said first controlling probe becomes greater than the potential of said reference probe due to ice formation around said first controlling probe and for turning off the refrigeration system when the potential of said second controlling probe becomes greater than the potential of said reference probe due to ice formation around said second controlling probe.

2. The apparatus of claim 1 wherein said constant current producing means produces alternating current so as to minimize electrolytic deposition on said probes.

3. The apparatus of claim 1 wherein said measuring means further comprises means for comparing the voltage potential of said first controlling probe with the potential of said reference probe and means for comparing the voltage potential of said second controlling probe with the potential of said reference probe.

4. The apparatus of claim 3 wherein both of said comparing means are electronic comparators and wherein the refrigeration system is operated in accordance with the output signals of the two comparators.

* * * * *